United States Patent
Zhang et al.

(10) Patent No.: US 10,195,245 B2
(45) Date of Patent: Feb. 5, 2019

(54) TETRAPEPTIDES DERIVED FROM HUMAN C-X-C CHEMOKINES USEFUL FOR TREATMENT OF VARIOUS SKIN CONDITIONS

(71) Applicant: Helix Biomedix, Inc., Bothell, WA (US)

(72) Inventors: Lijuan Zhang, Kenmore, WA (US); Robin Carmichael, Redmond, WA (US)

(73) Assignee: HELIX BIOMEDIX, INC., Bothell, WA (US)

( * ) Notice: Subject to any disclaimer, the term of this patent is extended or adjusted under 35 U.S.C. 154(b) by 0 days.

(21) Appl. No.: 14/907,811

(22) PCT Filed: May 14, 2014

(86) PCT No.: PCT/US2014/037978
§ 371 (c)(1),
(2) Date: Jan. 26, 2016

(87) PCT Pub. No.: WO2014/200651
PCT Pub. Date: Dec. 18, 2014

(65) Prior Publication Data
US 2016/0184384 A1 Jun. 30, 2016
US 2017/0007662 A2 Jan. 12, 2017

Related U.S. Application Data

(60) Provisional application No. 61/835,424, filed on Jun. 14, 2013.

(51) Int. Cl.
*A61K 38/07* (2006.01)
*A61K 8/64* (2006.01)
*A61Q 19/00* (2006.01)
*C07K 5/04* (2006.01)
*A61Q 19/08* (2006.01)
*A61K 38/00* (2006.01)

(52) U.S. Cl.
CPC ............... *A61K 38/07* (2013.01); *A61K 8/64* (2013.01); *A61K 38/00* (2013.01); *A61Q 19/00* (2013.01); *A61Q 19/08* (2013.01); *C07K 5/04* (2013.01); *A61K 2800/74* (2013.01)

(58) Field of Classification Search
None
See application file for complete search history.

(56) References Cited

U.S. PATENT DOCUMENTS 7,696,174 B2 4/2010 Harris et al.
2013/0109614 A1 5/2013 Cheng et al.

FOREIGN PATENT DOCUMENTS

| CN | 101472944 A | 7/2009 |
|---|---|---|
| CN | 101855235 A | 10/2010 |
| EP | 2452686 A2 | 5/2012 |
| JP | 2004-509148 A | 3/2004 |
| JP | 2007-1981 A | 1/2007 |
| RU | 2458069 C2 | 8/2012 |
| WO | WO 2009/126037 A1 | 10/2009 |

OTHER PUBLICATIONS

Hu, Y.-J., et al. Biochemistry (1999), 38; pp. 643-650.*
Dooley, C. T., et al. J. Biol. Chem. (1998), 273(30); pp. 18848-18856 (Year: 1998).*
Dooley, C. T., et al. Life Sci. (1993), 52; pp. 1509-1517 (Year: 1993).*
Udugamasooriya, D. G., et al. Chembiochem. (2008), 9(10); pp. 1587-1589 (Year: 2008).*
Elkins, J. M., et al. Protein Sci. (2007), 16; pp. 683-694 (Year: 2007).*
Kundu, B., et al. J. Bioorg. Med. Chem. Lett. (1998), 8; pp. 1669-1672 (Year: 1998).*
Songyang, Z., et al. Science (1997), 275; pp. 73-77.*
Purington, L. C., et al. ACS Chem. Biol. (2011), 6(12); pp. 1375-1381.*
PCTUS2014037978, International Search Report and Written Opinion, dated Nov. 3, 2014, 10 pages.
TW103120387, Office Action, dated May 13, 2015, 7 pages.
Fromes et al., "The tetrapeptide acetyl-serine-aspartyl-lysine-proline improves skin flap survival and accelerates wound healing," *Wound Repair and Regeneration*, vol. 14, No. 3 (May 1, 2006), pp. 306-312.
Wells et al., "Selectivity and Antogonism of Chemokine Receptors," *Journal of Leukocyte Biology*, vol. 59, No. 1 (Jan. 1, 2996), pp. 53-60.

(Continued)

*Primary Examiner* — Kevin S Orwig
(74) *Attorney, Agent, or Firm* — Seed IP Law Group LLP

(57) ABSTRACT

Tetrapeptides consisting of (I or V)-X1-K-X2, where X1 can be selected from E, Q or K, and X2 can be selected from M, F, I, W, or V, exhibit diverse bioactivities. They are multi-functional effector molecules to stimulate keratinocytes migration; neutralize the proinflammatory effect of bacterial cell wall components such as lipoteichoic acids of the Gram-positive *S. aureus*; and induce angiogenesis in cultured human umbilical vein endothelial cells. The down-regulation of pro-inflammatory condition was also demonstrated using SOR-300-FT psoriasis skin model for representative peptide. The bioactivity was also supported by gene profiling study upon treatment of normal skin tissues using EPIDERM™ skin substitutes. The inventive peptides with diverse bioactivities are useful for treating various skin conditions including, but not limited to, acute or chronic wounds, striae distensae, aging skin, hair control, inflammatory skins such as psoriasis, atopic dermatitis and rosacea and for unwanted hair removal or for conditions such as removal of skin tags.

11 Claims, No Drawings
Specification includes a Sequence Listing.

(56) References Cited

OTHER PUBLICATIONS

Personal Care Products Council, "Report of INCI Names (23867 records)," (426 pages) (Apr. 5, 2017).
Tokuriki et al., "Stability effects of mutations and protein evolvability," *Current Opinion in Structural Biology* 19: 596-604, 2009.

\* cited by examiner

SEQUENCE LISTING

```
<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: tetrapeptide from the CAG binding region of C-
      X-C chemokine

<400> SEQUENCE: 1

Ile Glu Lys Met
1

<210> SEQ ID NO 2
<211> LENGTH: 4
<212> TYPE: PRT
<213> ORGANISM: Artificial Sequence
<220> FEATURE:
<223> OTHER INFORMATION: tetrapeptide from the CAG binding region of C-
      X-C chemokine

<400> SEQUENCE: 2

Val Glu Lys Phe
1

<210> SEQ ID NO 3
<211> LENGTH: 4
<212> TYPE: PRT
<213> ORGANISM: Artificial Sequence
<220> FEATURE:
<223> OTHER INFORMATION: tetrapeptide from the CAG binding region of C-
      X-C chemokine

<400> SEQUENCE: 3

Ile Glu Lys Ile
1

<210> SEQ ID NO 4
<211> LENGTH: 4
<212> TYPE: PRT
<213> ORGANISM: Artificial Sequence
<220> FEATURE:
<223> OTHER INFORMATION: tetrapeptide from the CAG binding region of C-
      X-C chemokine

<400> SEQUENCE: 4

Ile Gln Lys Ile
1
```

```
<210> SEQ ID NO 5
<211> LENGTH: 4
<212> TYPE: PRT
<213> ORGANISM: Artificial Sequence
<220> FEATURE:
<223> OTHER INFORMATION: tetrapeptide from the CAG binding region of C-
      X-C chemokine

<400> SEQUENCE: 5

Ile Lys Lys Trp
1

<210> SEQ ID NO 6
<211> LENGTH: 4
<212> TYPE: PRT
<213> ORGANISM: Artificial Sequence
<220> FEATURE:
<223> OTHER INFORMATION: tetrapeptide from the CAG binding region of C-
      X-C chemokine

<400> SEQUENCE: 6

Ile Lys Lys Val
1

<210> SEQ ID NO 7
<211> LENGTH: 4
<212> TYPE: PRT
<213> ORGANISM: Artificial Sequence
<220> FEATURE:
<223> OTHER INFORMATION: tetrapeptide from the CAG binding region of C-
      X-C chemokine

<400> SEQUENCE: 7

Ile Lys Lys Leu
1
```

TETRAPEPTIDES DERIVED FROM HUMAN C-X-C CHEMOKINES USEFUL FOR TREATMENT OF VARIOUS SKIN CONDITIONS

This application claims the benefit of priority to U.S. Provisional Application No. 61/835,424, filed Jun. 14, 2013, which is herein incorporated by reference in its entirety.

FIELD OF THE INVENTION

The present invention relates to tetrapeptides having biological, cosmetic and therapeutic activity. Particularly, the invention relates to tetrapeptides derived from a conserved region of several C-X-C chemokines. These peptides have shown activity to promote cell migration, angiogenesis, neutralize bacterial cell component such LTA induced pro-inflammatory signals, and stimulate normal epiderm skin substitutes. The invention is further related to methods of using of these peptides to promote wound repair and treat various insults affecting the skin and other related body surfaces such as the oral cavity.

BACKGROUND OF THE INVENTION

Keratinocytes and dermal endothelial cells are the main source of soluble factors regulating healing of skin wounds and ulcers. Abnormalities due to decreased activities including growth factor production, angiogenic response, macrophage function, collagen accumulation, epidermal barrier function, and keratinocyte and fibroblast migration and proliferation, all contribute to defective wound healing. Growth factors and cytokines have been used in clinical settings for treating wounds. Examples include, but not limited to, PDGF (platelet-derived growth factor (Rees et al, 1999) and GM-CSF (granulocyte-macrophage colony stimulating factor) that have been shown to exert beneficial effects on wound healing in patients suffering from various wounds and chronic skin ulcers of diverse etiology including hydroxyurea-related leg ulcers (Stagno et al, 1999), venous leg ulcers (Da Costa et al, 1999), hemoglobinopathy-related ulcers (Voskaridou et al, 1999), and wounds resulting from amputation (Gaches et al, 1998). Also intradermal administration of GM-CSF to leprosy patients with skin lesions leads to enhanced wound healing and increased numbers and layers of keratinocytes (Kaplan et al, 1992; Braunstein et al, 1994).

Both growth factors and cytokines are proteins. Difficulties with the use of protein therapeutics to treat epidermal wounds are often related to the large size of the proteins involved. The complex structure and the cost of manufacture of natural proteins are prohibitive for wide clinical use. Stability and compatibility of such natural proteins in formulation are also a major concern. The poor penetration due to large size of natural proteins to reach the target layer of skin often reduce the efficacy and account for failed beneficial effects of protein therapeutics. To overcome these issues, short peptides that bear the activity of large proteins should fill the need of less expensive, cost effective production, and simple handling and manipulation. In addition, short bioactive peptides are better absorbed and retained by wound tissue due to less susceptibility to protease. The advantage of absorption characteristics of short bioactive peptides also make them viable option for uses beyond the care of acute and chronic wounds, such as for treatment of the skin problems associated with aging and sun exposure.

Chemokines are structurally related and represent a large superfamily of 8 to 150 kd proteins that possess diverse biological activities. They are usually secreted upon cell stimulation to control leukocytes trafficking during homeostasis, as well as during inflammation, and are necessary for the linkage between innate and adaptive immunity. Along with adhesion molecules such as integrins and selectins, chemokines and their receptors act primarily as part of a complex molecular network that facilitates the selective movement of specific cell types into, and out of, targeted tissue microenvironment (Key et al., 2003; Ono et al., 2003). Chemokines selectively mediate the regionally specific recruitment of neutrophils, macrophages and lymphocytes. In addition to being chemotactic factors, the chemokines also play important roles in maintenance of homeostasis, angiogenesis/angiostasis, cellular differentiation and activation, wound healing, tumor growth and metastasis, lymphocyte homing and development of lymphoid tissue, and influencing the overall type 1/type 2 balance of immune response (Behm et al., 2012; Gillitzer et al., 2001; Raman et al., 2011; Romagnani et al., 2004; Rossi et al., 2000).

Defined by a tetra cysteine motif, the chemokines are subdivided into four distinct families according to the configurations of the cysteine residues at their amino terminus. There are two large subfamilies, CCL subfamily (CCL1 through CCL28) and CXCL subfamily (CXCL1 through CXCL16), as well as two small subfamilies, XCL subfamily (XCL1 through XCL2) and CX3CL1 subfamily (Bacon et al. 2003). The CXC subfamily of chemokines plays an important role in diverse processes, including inflammation, wound healing, growth regulation, angiogenesis, and tumorigenesis (Keeley et al., 2008; 2011). Many chemokines interact with the glycosaminoglycan (GAG) moieties of proteoglycans on endothelial cells and the extracellular matrix (Handel et al., 2005). Heparin, which serves as a model compound for heparin sulfate, is the most ubiquitous class of GAG that is expressed on virtually every cell in the body. All chemokines interact with heparin GAG.

In our studies we noted the C-X-C chemokines showed some sequence similarities in their primary amino acid sequences although highly conserved in the secondary structures. Examination of the primary amino acid sequences of nine human C-X-C chemokines reveals a highly conserved region located at the C-terminal portion which is involved in GAG binding using the NCBI accession number of each chemokines shown below in "Detailed description of the invention, 1$^{st}$ paragraph". We generated tetrapeptides from the GAG binding region and tested the bioactivity. To our surprise the tetrapeptides showed diverse bioactivities including promote keratinocyte migration, induce angiogenesis on human umbilical vein endothelial cells, neutralize LTA induced pro-inflammatory cytokines, and modulating cell growth and growth factor production. The tetrapeptides are useful as both pharmaceutical and cosmetic products for improving various skin conditions.

SUMMARY OF THE INVENTION

The present invention relates to short bio-active peptides that are useful for promoting wound healing in mammals. The wounds preferably targeted by the isolated peptides are those affecting the skin and associated mucosal surfaces. Though not to be limited to any particular mechanism, the inventive peptides are able to effect wound healing by stimulating cell migration and angiogenesis. The inventive peptides are useful in both in vitro and in vivo manners, and are able to induce the aforementioned activities in keratinocytes.

One embodiment of the present invention is drawn toward isolated tetrapeptides of the formula (I or V)-$X_1$-K-$X_2$, where X1 can be selected from E, Q and K; and X2 can be selected from M, F, I, W, V, and L. The isolated peptides may contain either L- or D-enantiomeric forms of amino acids, or combination thereof. According to yet another embodiment of the invention, the isolated peptides may be conjugated to a carrier protein, or modified via C-terminal amidation or N-terminal acylation with fatty acids (i.e. lipidation). These additions enhance the bio-activity of the peptides when applied to skin and wounds thereof.

According to certain preferred embodiments of the current invention, the isolated peptides all contain a lysine at position 3. Specific embodiments of the isolated peptides comprise SEQ ID NO: 1, 2, 3, 4, 5, 6 and 7 all of which show stimulatory activities towards cell migration and effect wound repair.

The tetrapeptides derived shown below fit into the formula (I or V)-$X_1$-K-$X_2$, where X1 can be selected from E, Q and K; and X2 can be selected from M, F, I, W, V, and L.

| SEQ ID NO. | HB NO. | Sequence |
|---|---|---|
| 1 | HB2233 | IEKM |
| 2 | HB2267 | VEKF |
| 3 | HB2270 | IEKI |
| 4 | HB2271 | IQKI |
| 5 | HB2272 | IKKW |
| 6 | HB2273 | IKKV |
| 7 | HB2274 | IKKL |

Another embodiment of the present invention is drawn toward therapeutic or cosmetic compositions which contain a pharmaceutically or cosmetically acceptable carrier and one or more of the aforementioned peptides. The aforementioned compositions are useful for the manufacture of medicament or cosmetic compositions for use in application for healing skin wounds of mammals. The peptide in such compositions preferably ranges in concentration from about 0.1 µg/mL to about 500 µg/mL, or from about 0.1 µg/mL to about 20 mg/mL. Preferred forms of the composition are aerosols, emulsions, liquids, solutions, lotions, creams, pastes, ointments, powders, gels and foams.

Additionally, the peptides of the present invention, and compositions containing them, may provide useful features for inclusion in general skin care and cosmetic formulations, such as various skin cosmetics, skin creams, lotions, sunscreens, and therapeutic lotions or creams such as anti-acne formulations for post laser procedure care.

The present invention is also directed towards methods of using the aforementioned compositions for healing wounds in mammals. Typically, the treatment method entails administering an effective amount of peptide-containing compositions to wounds and or inflammatory conditions, especially those of the skin (epidermis) and associated mucosal tissues, for an effective amount of time. Such wounds include surgical wounds, abrasions, blisters, burns, lacerations, ulcers, bruises, rashes, scars, stretch marks and skin damage due to intrinsic and extrinsic effects of aging and environmental exposure, including wrinkling, skin sagging and photo-damage. Inflammatory skin conditions include psoriasis, atopic dermatitis and rosacea and inflammation arising from hair removal.

DETAILED DESCRIPTION OF THE INVENTION

Chemokines modulate wound healing, inflammatory/anti-inflammatory and angiogenic/angiostatic activities. They exert their function by binding to the G-protein coupled receptor (GPCR) class of receptors on leukocytes and cell surface glycosaminoglycans (GAGs) in target tissues. The binding of chemokines to GAGs is mediated through ionic forces generated by the interactions of negatively charged chains on GAGs with clusters of basic residues in the chemokines (Handel et al., 2005). In vivo, the situation is more complicated, and it has been proposed that chemokines work by producing immobilized or haptotactic gradients, which direct the migration of cells to the sites of inflammation (Proudfoot, 2006). The GAG-chemokine interactions may play a pivotal role in the establishment of gradients along the extracellular matrix and may facilitate the binding of the chemokines to their G-protein-coupled receptors. GAGs or heparin sulfate (HS) proteoglycans can also behave as functional chemokine coreceptors for signaling, leading to the formation of a ternary complex of GAG/chemokine and chemokine receptor (Handel et al. 2005). Studies on specific chemokines have mapped the binding sites of the GAGs to the chemokines. In close examination of the primary amino acid sequence of the conserved GAG binding site of nine human C-X-C chemokine precursor proteins including GRO-alpha precursor (CXCL-1), chemokine 2 precursor (CXCL-2), chemokine 3 precursor (CXCL-3), chemokine 4 precursor (CXCL-4), chemokine 5 precursor (CXCL-5), chemokine 6 precursor (CXCL-6), IL-8 precursor (CXCL8), chemokine 9 precursor (CXCL-9), chemokine 11 precursor (CXCL-11), we found a conserved tetrapeptide region that is of particular interesting. The conserved tetrapeptide stretch defined in this study is located within a partial GAG binding region. Below is a schematic illustration of alignment of the C-terminal sequences of selected human C-X-C chemokine precursors and highlight of the conserved short tetrapeptide. The alignment is generated using the COBALT program for multiple protein sequences alignment on the NCBI's website (ncbi.nlm.nih.gov). Only the C-terminal portion of each chemokines in the alignment is shown and the numbers are the start and end of the residues in the sequences. A. GRO-alpha precursor (NCBI accession number P09341.1); B. chemokine 2 precursor (NCBI accession number NP_002080.1); C. chemokine 3 precursor (NCBI accession number NP_002081.2); D. chemokine 4 precursor (NCBI accession number P80162.4); E. chemokine 5 precursor (NCBI accession number NP_002985.1); F. chemokine 6 precursor (NCBI accession number NP_002984.1); G. IL-8 precursor (NCBI accession number); H. chemokine 9 precursor (NCBI accession number NP_002407.1); I. chemokine 11 precursor (NCBI accession number EAX05774.1).

```
        Re-                                                  re-
        si-                                                  si-
        due                                                  due
        start                                                end 74    VIATLKNGR-KACLNPASPIVKKIIEKMLNSD-KSN  107
   B.   74    VIATLKNGQ-KACLNPASPMVKKIIEKMLKNG-KSN  107
   C.   74    VIATLKNGK-KACLNPASPMVQKIIEKILNKG-STN  107
   D.   72    LIATLKNGR-KICLDLQAPLYKKIIKKLLES-----  101
   E.   80    VVASLKNGK-EICLDPEAPFLKKVIQKILDGGnKEN  114
   F.   80    VVASLKNGK-QVCLDPEAPFLKKVIQKILDSGnKKN  114
   G.   66    IIVKLSDGR-ELCLDPKENWVQRVVEKFLKRA-ENS   99
   H.   63    IIATLKNGV-QTCLNPDSADVKELIKKWEKQVsQKK  125
   I.   62    VIITLKENKgQRCLNPKSKQARLIIKKVERKNf---   94
                      *  * *       *  * *  *-*--*
   Consensus                               I-K-
```

Shown in the alignment is a short tetrapeptide motif that is highly conserved among CXC chemokines. * indicates a partial GAG binding site of chemokines. The tetrapeptides show a conserved backbone of I-K-. Except IL-8 that has a valine (V) all others have an isoleucine (I) in position 1 and a lysine (K) in position 3 of the tetrapeptide motif. Therefore (I or V)-$X_1$-K-$X_2$ formula can be used to represent the tetrapeptides generated and shown in Table 1. It is worth noting that the GAG binding region of the chemokines is also involved in dimer formation as most CXC chemokines reversibly exist as monomers and dimers, and so, the recruitment profile would be influenced not only by the monomer-dimer equilibrium constant but also by the binding interactions of monomer and dimer to receptors on neutrophils and to GAGs on cell surface and interstitial space in the target tissue (Gangavarapu et al., 2012).

The tetrapeptides derived shown below fit into the formula I(V)-$X_1$-K-$X_2$, where X1 can be selected from E, Q and K; and X2 can be selected from M, F, I, W, V, and L.

| SEQ ID NO. | HB NO. | Sequence |
|---|---|---|
| 1 | HB2233 | IEKM |
| 2 | HB2267 | VEKF |
| 3 | HB2270 | IEKI |
| 4 | HB2271 | IQKI |
| 5 | HB2272 | IKKW |
| 6 | HB2273 | IKKV |
| 7 | HB2274 | IKKL |
| 8 | HB2268 | KMG |

C-X-C chemokines are well known for their chemotactic activity toward many cell types. To assess whether the newly derived tetrapeptides possess the activity to stimulate keratinocytes migration, SEQ ID NOs 1, 2, 3, 4, 5, 6, 7 and 8 were subjected to keratinocyte scratch wound test, an assay well accepted for assessing the ability of active compound to induce cell migration and wound closure in vitro. The experiment was performed in the serum-free keratinocyte growth medium in the absence of supplement in order to restrain cells proliferation. The wounded area was examined by phase-contrast microscopy at the indicated times. As shown in Table 1, the tetrapeptides significantly induce the scratch wound closure. At 20 µg/ml, the percentage of wound closure induced by SEQ IDs 1, 2, 3, 4, 5, 6 and 7 ranges from 165% to 240% compared to that of PBS treated which was taken as 100% (Table 1). A randomly generated peptide SEQ ID NO 8 does not induce cell migration and scratch wound closure. To confirm that the peptides are not toxic to the keratinocytes at the concentrations tested for scratch wound closure all peptides were subjected to the MTT cytotoxicity test. None of the peptides were cytotoxic to normal skin keratinocyte in vitro after 24 hrs incubation at concentrations up to 500 ug/ml. In conclusion, treatment with tetrapeptides SEQ ID NOs 1-7, significantly induced migration of normal human epidermal keratinocyte cells into the scratch area as indicated by the percentage of closure of the wounded area after 7 hr treatment in comparison to that of PBS treated control cells.

Angiogenesis, the formation of new capillaries from the pre-existing vascular network, is an essential step of wound repair. The peptides generated in the current invention, SEQ ID NOs 1-7, also stimulate capillary tube formation. The in vitro angiogenesis assay uses human umbilical vein endothelial cells (HUVEC) to measurer a series of events that lead to forming new capillary tubes. Upon induction, the HUVEC undergoes migration to align then sprouting from individual cells. The sprouting event leads to formation of new capillary tubes which further develop to form closed polygons. Eventually a complex mesh like structure is developed. Human cathelicidin peptide, LL-37, is a well-studied example to promote angiogenesis. It is used as positive control in the assessment. The sprouting of new capillary tubes becomes visible just after 3 hr treatment with LL-37 (Table 2). After 5 hr treatment with LL-37, the closed polygons are formed. Compared to LL-37, SEQ ID NOs. 1, 2, 3, 4, 5, 6, and 7, induced similar changes on HUVEC resulting in new capillary tube formation and complex polygon structures at 3 and 5 hr treatment (Table 2). In contrast, the randomly generated peptide SEQ ID NO 8 (KMG) and PBS do not induce such change at the time the angiogenic activity was observed for LL-37 and the inventive peptides (Table 2).

The Gram-positive cell wall component peptidoglycan (PGN) is well known to stimulate pro-inflammatory cytokine expression. Lipoteichoic acid (LTA) is the key molecule in PGN that causes a concentration- and time-dependent increase in pro-inflammatory signals including nitric oxide synthase (iNOS), cyclooxygenase-2 (COX-2), IL-1 beta, TNF-alpha and IL-6 up-regulation (Lin et al., 2010). We therefore pretreated LTA with the inventive peptides and then assess the IL-6 stimulatory activity upon contact with human skin keratinocytes. As shown in Table 3, pretreatment of LTA with SEQ ID NOs 1, 2, 3, 4, 5, 6, and 7 significantly reduce the level of LTA stimulated IL-6 expression in human skin keratinocyte culture, suggesting the peptides can neutralize the toxic effect of free LTAs. It is very likely that the positively charged residues of the tetrapeptides bind to the negatively charged LTA thus blocking the interaction of LTA with its receptors. This is significant as bacterial cell wall components have been implicated in inflammatory skin conditions such as acne, rosacea, atopic dermatitis etc.

Modulation of cell proliferation is another important step in wound repair. We tested the inventive peptide for proliferative activity on human skin keratinocytes. Compared to the chemotactic activity measured in the scratch test, angiogenesis and blocking LTA induced IL-6 expression the inventive peptides showed various yet moderate activities on modulation of keratinocyte proliferation. SEQ ID NO 1 (HB2233) showed inhibitory activity on keratinocyte proliferation, such inhibitory activity was also observed for SEQ ID NO 3 (HB2270). SEQ ID NO 6 seems to stimulate keratinocyte proliferation but such activity is only marginal. The inhibitory activity on keratinocyte proliferation prompts us to test TGF-β1 expression as this growth factor is well known for inhibiting cell proliferation. As shown in Table 4, both SEQ ID NO 1 and 3 induced moderate level of TGF-β1 expression in cultural keratinocytes.

SOR-300-FT, developed by MatTek Corporation (Ashland Mass.), is a highly differentiated in vitro psoriasis tissue comprised of normal, human-derived keratinocytes and psoriatic fibroblasts Morphologically, the tissue is of uniform thickness and it expresses increased levels of hyperproliferated cells as well as pro-inflammatory markers such as psoriasin, elafin, human beta-defensin-2, and LL-37 etc (Ayehunie et al., 2012). The pro-inflammatory condition of the tissue prompts us to test the inventive peptides to see if they modulate the inflammatory response. Due to the high cost of the tissue model, a representative peptide SEQ ID NO 1, HB2233, was selected as a proof of concept study using SOR-300-FT tissue model. The SOR-300-FT tissues were treated with HB2233 in duplicate at 200 µg/ml. Total 12 gene markers associated with psoriasis condition are studied. The study was run in parallel with calcipotriol. qPCR analysis revealed that after 72 hr treatment SEQ ID NO 1 (HB2233) significant down-regulates the expression level of LL-37 (3.7 fold) which is overexpressed in inflamed psoriasis skin (Table 5). The psoriasis drug calcipotriol significantly downregulates HBD-2 (9.0 fold) and psoriasin (2.3 fold). Both HB2233 and calcipotriol down-regulate Ki67 expression which is responsible for the hyperproliferation and early maturation of keratinocytes in psoriasis skin. In addition, SEQ ID NO 1 (HB2233) also down-regulates CXCL1 (GRO alpha) and CXCL5 (ENA-78) expression both of which are significantly up-regulated in psoriasis skin compared to normal healthy skin (Ayehunie S., 2012), however, calcipotriol does not seem to affect the level of both genes. This clearly suggests HB2233 could be a novel therapeutic that functions via a different mechanism from that of the current drug calcipotriol for the treatment of inflammatory skin conditions such as psoriasis.

To better understanding how the same peptide affects normal healthy skin tissues we put SEQ ID NO:1, HB2233, to a gene profiling study performed by Sunny Biodiscovery (Santa Paula, Calif.) using EPIDERM™ normal human skin substitutes, purchased from MatTek Corporation (Ashland, Mass.). The skin substitutes were equilibrated for overnight prior to treatment with peptide or water control in duplicates for 24 hrs. At the end of treatment RNA was extracted and subjected to PCR array analysis. As shown in Table 6, SEQ ID NO 1, HB2233, stimulates genes that are involved in ECM synthesis (collagen and integrins). As expected it modulates chemokines (CXCL11 and MAPK3 etc) and growth factors (TGF-β1 and VEGF etc.). The gene profiling study supports the activity observed in vitro that the inventive peptides modulate of cell proliferation, angiogenesis and wound healing activities.

All the peptides included in the current invention were synthesized using standard Fmoc (9-fluorenylmethoxycarbonyl) solid-phase chemistry. The peptides can be prepared as either amidated or free acid sequences using standard amino acids. Amidation of the carboxy-terminus may render the inventive peptides less susceptible to protease degradation and increase their solubility compared to the free acid form, therefore providing heightened therapeutic potency. The peptides can comprise L- or D-amino acid enantiomers, either containing residues of one enantiomeric form or a combination of both forms. The peptides may be modified on both the N-terminus and the C-terminus. For example, it is discussed that N-terminus lipidation or aceylation may improve peptide penetration across skin without altering the bioactive function of the peptide (Samah, 2011). Therefore the peptides may also be lipidated which may provide for enhanced skin penetration. Examples of saturated or unsaturated fatty acids that can be used to provide the C12-18 lipid-component of the compounds of the invention include lauric acid, myristic acid, palmitic acid, stearic acid, myristoleic acid, palmitoleic acid, oleic acid and linoleic acid. The carboxy-terminus of the peptides can be modified with acidic (—COOH) or amidated (e.g., —CONH2, —CONHR, or —CONR2). Amidation of the carboxy-terminus may render the inventive peptides less susceptible to protease degradation and increase their polarity compared to the free acid forms, therefore providing heightened therapeutic potency. Also the peptide functional groups that may typically be modified include hydroxyl, amino, guanidinium, carboxyl, amide, phenol, imidazol rings or sulfhydryl.

Peptides may also be conjugated to soluble or insoluble carrier molecules to modify their solubility properties as needed and to increase the local concentrations of peptides in targeted tissues. Examples of soluble carrier molecules include, but not limited to, polymers of polyethyleneglycol (PEG) and polyvinylpyrrolidone; examples of insoluble polymers include, but not limited to, silicates, polystyrene, and cellulose. Peptides may be micro-encapsulated using liposome technology or via nano-technology to enhance their stability and for controlled release. General to the above protocol, the peptides may be produced using any method known to those skilled in the art such as those disclosed in Merrifield (*J Am Chem Soc.* 85:2149, 1963); Carpino et al. (*J Org Chem.* 51:3732, 1986); Merrifield et al. (*Anal Chem.* 38:1905, 1966); or Kent et al. [*High Yield Chemical Synthesis Of Biologically Active Peptides On An Automated Peptide Synthesizer Of Novel Design*, IN: PEPTIDES 1984 (Ragnarsson, ed.) Almqvist and Wiksell Int., Stockholm (Sweden), pp. 185-188], all of which are herein incorporated by reference in their entirety.

The current invention is directed towards methods of using the above described peptides, such as in formulations or as therapeutic agents. These methods may involve the use of a single peptide, or multiple peptides in combination. In certain instances, the inventive composition can be disposed within devices placed upon, in, or under the skin. Such devices include transdermal patches, implants, and injections which release the substances in such a manner as to contact the skin or hair follicle either by passive or active release mechanisms. The compositions used to deliver the peptides in the methods described herein can be in the form of an aerosol, emulsion, liquid, lotion, solution, gel, micro-encapsulation, cream, paste, ointment, powder, foam, or other pharmaceutically acceptable formulation. Furthermore, the peptides can be delivered using less involved formulations such as deionized/distilled water, PBS or standard medical saline solutions.

The formulation may optionally have cosmetic appeal, and/or contain other agents such as retinoids, vitamin C or other peptides that can act as adjuvant for the therapeutic action of the inventive peptides. Antibiotics can also be added to the formulation in order to ward off infection, thereby permitting maximal healing processes to occur.

The formulation may contain protease inhibitors. A protease inhibitor can be selected to specifically target proteases that would be expected to degrade the selected bioactive peptide; such a selection would be determined based on the length and/or sequence of the bioactive peptide. However, protease inhibitors need not necessarily be selected in any specific manner; for example, a protease inhibitor cocktail, which contains two or more inhibitors, can be employed in the instant invention. The following types of protease inhibitors can be incorporated in the invention: serine protease inhibitors, cysteine protease inhibitors, aspartate protease inhibitors, metalloproteinase inhibitors, thiol protease inhibitors and threonine protease inhibitors. The protease inhibitor used in the invention may be a peptide or protein or chemicals. Non-limiting examples of such inhibitors are the serpins, which include alpha-1-antitrypsin, complement 1-inhibitor, antithrombin, alpha-1-antichymotrypsin, plasminogen activator inhibitor 1, and neuroserpin, or chemicals including, but not limited to, ursolic acid and tranexamic acid that can act as adjuvant for the therapeutic action of the inventive peptides.

Generally, a pharmaceutically acceptable formulation would include any carrier suitable for use on human skin. Such pharmaceutically and cosmetically acceptable carriers include ethanol, dimethyl sulfoxide, glycerol, silica, alumina, starch, and equivalent carriers and diluents. The formulation may optionally have cosmetic appeal, and/or contain other agents such as retinoids or other peptides that can act as adjuvants for the therapeutic action of the inventive peptides. Antibiotics can also be added to the formulation in order to ward off infection, thereby permitting maximal healing processes to occur. The concentration of the peptide in the composition can be about 0.1 µg/mL to about 500 µg/mL or about 0.1 µg/mL to about 10%; however, the ultimate concentration employed may vary outside these ranges, depending on the nature of the wound/tissue condition, the bio-activity of the inventive peptide and the use of any adjuvant or technique to obtain enhanced composition absorption. The CTFA Cosmetic Ingredient Handbook, Second Edition (1992) describes a wide variety of non-limiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g. clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants, binders, biological additives, buffering agents, bulking agents, chelating agents, chemical additives, cosmetic biocides, denaturants, drug astringents, external analgesics, film formers or materials, opacifying agents, pH adjusters, propellants, reducing agents, sequestrants, skin bleaching and lightening agents (e.g. hydroquinone, kojic acid, ascorbic acid, magnesium ascorbyl phosphate, ascorbyl glucosamine), skin-conditioning agents (e.g. humectants), skin soothing and/or healing agents (e.g. panthenol and its derivatives, aloe vera, pantothenic acid and its derivatives, allantoin, bisabolol, and dipotassium glycyrrhizinate), skin treating agents, thickeners, and vitamins and derivatives thereof.

The administration of the inventive peptides and associated compositions may be made to humans and animals, including all mammals. Application may also be made in combination with typical and/or experimental materials such as tissue grafts, skin substitutes, tissue culture products and dressings. Examples include, but not limited to, gauzes (woven and non-woven, impregnated, nonadherent, packing, debriding); compression bandages and system; wound fillers and cleansers; contact layers; collagens; amniotic membranes; acellular human dermis; acellular matrices and combination products; and various commonly used dressings.

List of Commonly Used Dressings

| Categories of Wound Dressings | Products |
|---|---|
| Films | BIOCLUSIVE ™ (Johnson & Johnson Medical, Inc) |
|  | OMIDERM ™ (Omicron Scientific Ltd.), |
|  | OPSITE ® (Smith & Nephew United, Inc) |
|  | POLYSKIN ®II transparent dressing (Kendall Healthcare) |
|  | TEGADERM ™ (3M Health Care) |
| Hydrogels | INTRASITE ™ (Smith & Nephew United, Inc), |
|  | NU-GEL ™ (Johnson & Johnson Medical, Inc.) |
|  | VIGILON ® (Bard Medical Division) |
| Hydrocolloids | COMFEEL ® (Coloplast Sween Corp.) |
|  | DUODERM ® (ConvaTec) |
|  | RESTORE ™ (Hollister Incorporated) |
| Polysaccharides | BARD ® Absorption Dressing (Bard Medical Division) |
|  | DEBRISAN (Johnson & Johnson Medical, Inc.) |
|  | DUODERM ® Granules (ConvaTec) |
| Alginates | KALTOSTAT ® (ConvaTec) |
|  | SORBSAN ™ (Dow Hicham Pharmaceuticals Inc) |
| Foam Dressings | ALLEVYN ® (Smith & Nephew United, Inc) |
|  | LYOFOAM ® (Acme United Corporation) |
| Laminates | BIOBRANE ® (Dow Hickam Pharmaceuticals Inc) |

In general, the composition can be administered topically, orally, transdermally, systemically, or by any other method known to those of skill in the art to be useful to deliver the inventive peptides to the target tissue. Compositions may also be applied in an in vitro or ex vivo manner, either to cells or patient grafts growing in culture, for example.

The compositions of the present invention may contain one or more additional agents that exert skin care activity. Beside the bioactive peptide component, the instant invention can contain other active agents such as hyaluronic acid, niacinamide, phytantriol, farnesol, bisabolol, salicylic acid, retinol, retinoic acid, alphahydroxy acids, ascorbic acid and alguronic acid. It is expected that certain additional active agents will act synergistically with the bioactive peptide component, or will enhance the shelf-life of the formulation.

Further, the abbreviations for the amino acids follow conventional usage:

| Alanine | Ala | A |
| Arginine | Arg | R |
| Asparagine | ASN | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |

| Threonine | Thr | T |
| Tryptophan | Trp | W |
| Tyrosine | Tyr | Y |
| Valine | Val | V |

Details on techniques for formulation and administration of pharmaceuticals may be found in the latest edition of Remington's Pharmaceutical Sciences (Mack Publishing Co, Easton Pa.). Although local topical delivery is desirable, there are other means of delivery, for example: oral, parenteral, aerosol, intramuscular, subcutaneous, transcutaneous, intramedullary, intrathecal, intraventricular, intravenous, intraperitoneal, or intranasal administration. The present invention can be formulated in a number of carrier vehicles, for example, in a spray; an aerosol; a water and an oil-type emulsion; an oil and water-type emulsion; a face cream or body cream; a sun lotion or after-sun lotion; or other topical administration vehicle. Additionally, the peptides of the present invention, and compositions containing them, may provide useful features for inclusion in general skin care and cosmetic formulations, such as various skin cosmetics, skin creams, lotions, sunscreens, and therapeutic lotions or creams such as anti-acne formulations.

Areas of Application

The peptides of the current invention may be used for treating wounds of the skin. Skin and mucosal tissue damage occurs when the epidermal layer is breached, such as from a laceration, burn or blister. Injury can also involve crushing or bruising, which involves tissue damage without concurrent fissure of the epidermis. Skin infections as well as certain chronic illnesses such as cancer and autoimmune diseases can also exact a toll on epidermal surfaces. Ulcers such as those affecting diabetes or those associated with pressure sores, are another form of skin damage; these wounds are often quite intractable, being inflamed, prone to infection, and requiring a length healing process. The persistence of an ulcer or other type of chronic wounds is due to a failure of cellular processes involved in healing and new blood vessel generation due to impaired ability for angiogenesis. Angiogenesis is the process of formation of new capillary network (microvascular) in response to hypoxia or other stimuli (Folkman et al., 1992). The process involves the local secretion of angiogenic factors from both hypoxic endothelium and supporting pericytes that induce endothelial proliferation and sprouting of neovessels. Insufficient angiogenesis contributes to impaired wound healing and skin ulcers (Galiano et al., 2004). The failure in wound healing may also be a result of inability to epithelialize the lesion partially due to the fact that the keratinocytes at the wound border do not migrate to close or cover the sore (Enoch and Price, 2004). Healing of skin and mucosal wounds is orchestrated, in part, through the activation of basal keratinocytes. Upon activation the keratinocytes located at the wound perimeter migrate to form a single layer over the wound in a process referred to as epithelialization. It has been shown that keratinocytes at the non-healing edge of chronic wounds are hyperproliferative but non-migratory, and lack of migration leads to inability to epithelialize and plays an important role in pathogenesis of chronic ulcers (Harsha et al., 2008). The current invention may also be used to treat damages associated with keratinocytes in skin and mucosal tissues. The term "associated mucosal tissues" relates to any tissue organized in a manner similar to the skin and contains epithelial cells/keratinocytes including, but not limited to, the inner-lining surfaces associated with the mouth, nose, throat, ear, anus, genitalia and the palpebral conjunctive of the eye. Examples of wounds or lesions/injuries that can affect these tissues and are amenable to treatment with the inventive peptides are abrasions, blisters, burns, lacerations, punctures, ulcers, bruises, rashes and scars. Post-surgical trauma can also be treated with the peptides.

Another form of epidermal damage is subtle and results over a long period of time, eventually compromising skin function, so called aging skin. There are two main processes that induce skin aging; intrinsic (chronological aging) in sun protected skin and extrinsic (photo-aging) in sun-exposed areas. Intrinsic aging reflects the genetic background and depends on time. Regardless, aging skin shares with one or more of the following: wrinkles, fine lines, hyperpigmentation, erythema, loss of radiance, smoothness, firmness, skin tone clarity and evenness, and alterations in pore appearance. Underlying these visible signs are various histological and cytological changes induced by acute or chronic exposure of environmental stimuli such as ultraviolet (UV) and pollutions in addition to genetic predisposition. Cosmetic problems such as wrinkling, dryness, thinning, sagging and greater susceptibility to bruising are usual outward signs of epidermal damage that, in addition to aging, may also occur prematurely due to prolonged exposure to damaging agents such as ultraviolet rays and pollutions. Therefore the disclosed peptides may be used towards problems associated with aging skin caused by both intrinsic and extrinsic stimuli, to prevent and repair the damage therefore to regenerate healthy skin tissue to reverse the effects of aging. In a related manner, the peptides could be applied to tissue that had been damaged by exposure to various external agents such as sunlight. The invention can also be used as a cosmetic in these regards to render a more youthful appearance and texture. The short peptides by themselves unaltered, or via chemical modification and/or specialized delivery, can be made to penetrate through the epidermis to affect processes counter to those that cause skin thinning, wrinkles, fragility and roughening/hardening. As the keratinocytes are the main component of epidermal surfaces and are diminished in aged and damaged skin, replenishment thereof by peptide stimulation is expected to reverse the aforementioned problem.

Skin is relatively elastic, but there are limits to its capacity to stretch. Stretch marks, or striae, are a form of scarring on the skin with an off-color hue. They are caused by tearing of the dermis, which over time may diminish, but will not disappear completely. They first appear as reddish or purple lines, but tend to gradually fade to a lighter range. Stretch marks are often the result of the rapid stretching of the skin associated with rapid growth or rapid loss of weight. Stretch marks can appear anywhere on body sites that do not undergo notable or excessive stretching or distention at all. Most common places are the abdomen, breasts, upper arms, underarms, back, thighs, hips, and buttocks. The stretch marks are often caused by the hormonal changes of some major stages of life like puberty and pregnancy, but corticosteroid treatment, obesity, aesthetic surgery and intensive body building may lead to stretch marks. Under the action of corticosteroids the growth of both keratinocytes and fibroblasts can be severely damaged and consequently the synthesis of collagens I and III as well as fibronectin synthesis is also significantly reduced up to over 90% compared to normal skin (Rogalski et al., 2002). It has been shown that combination of high-dose corticosteroids and anti-vascular endothelial growth factor (antiangeogenesis) therapy can worsen the striae condition and should be avoided (Wheeler et al., 2012). Repair and restore the function of keratinocytes in the dermal/epidermal section could be the key to stretch mark correction. The peptides of the current invention that promote scratch wound closure and stimulate angiogenesis essential for wound healing are therefore ideal for treatment of stretch marks.

Keratinocytes produce and secrete antimicrobial peptides (AMPs) which function as endogenous antibiotics and as signaling molecules within the cutaneous innate immune system. AMPs are the key component of the host innate immune defense system and provide the first line of defense and killing of pathogenic microorganisms. In addition they also modulate and modify host inflammatory responses by a variety of mechanisms. However, abnormal expression of these peptides has been associated to the pathogenesis of inflammatory skin diseases. Recent studies imply that LL-37 may play an important role in the pathogenesis of psoriasis and rosacea.

Psoriasis is a chronic inflammatory skin disease that affects approximately 2% of the general population (Lowes et al, 2007). Psoriasis is characterized by accumulation of Th1-type T cells and neutrophils, keratinocyte hyperproliferation and differentiation, and enhanced epidermal production of AMPs. In psoriatic lesions, many AMPs are highly expressed such as cathelicidin (LL-37), β-defensins, S100 proteins, chemokines, RNase 7, lysozyme, elafin, neutrophil gelatinase-associated lipocalin, and so forth. In particular, the cathelicidin LL-37 is overexpressed in inflamed skin in psoriasis, binds to extracellular self-DNA released from dying cells and converts self-DNA to a potent stimulus for plasmacytoid dendritic cells (Dombrowski et al., 2012). Although it is controversy about the role of LL-37 in psoriasis, it is evident that this peptide induces keratinocyte proliferation and production of proinflammatory cytokines in cultured keratinocytes. In addition to psoriasis, LL-37 has recently been implicated in the development of systemic lupus erythematosus and rheumatoid arthritis (RA). LL-37 is highly expressed in the skin of systemic lupus erythematosus patients (Sun et al., 2011). In RA, neutrophil granulocytes fuel inflammation and damage tissue in the joint by releasing cytotoxic agents, AMPs, proteases and other inflammatory mediators. It was shown in animal model that LL-37 is strongly upregulated in RA synovial membranes and in joints from rats with arthritis as compared with healthy joints (Hoffmann et al., 2012). The observation that HB2233 significantly down-regulate the expression of LL-37 as well as several other factors highly associated with inflammation suggests that the inventive peptides could be potential therapeutics for inflammatory conditions including, but not limited to, psoriasis, systemic lupus erythematosus and rheumatoid arthritis.

Rosacea is one of the most common dermatoses of adults. Current concepts suggest that known clinical trigger factors such as UV radiation, heat, cold, stress, spicy food, and microbes modulate Toll-like receptor signaling, induce reactive oxygen species, as well as enhance AMPs and neuropeptide production (Kenshi et al., 2009; Yamasaki et al., 2009). Excess of cathelicidin in the form of LL-37 was reported in rosacea which appears to result from the abnormal function of innate immune pattern recognition by TLRs, and proteases that process hCAP18 (Yamasaki et al., 2007; 2011). Similar to psoriasis and systemic lupus erythematosus, the excess presence of LL-37 in rosacea has been speculated to enable recognition of self-nucleic acids by both plasmacytoid dendritic cells and keratinocytes which may exacerbate inflammation thus contributing to disease by permitting auto-inflammatory signaling (Gilliet et al., 2008; Ganguly et al., 2009). Down-regulation of LL-37 in SOR-300-FT skin tissues by the inventive peptides supports a promising and potentially useful treatment for improving LL-37 associated inflammatory condition in rosacea.

In addition to inflammatory skin conditions, higher levels of LL-37 are also associated with several aggressive solid tumor types. It was shown that LL-37 is over-expressed progressively in human prostate tumors as the Gleason score increases and in bone metastasis (Jonathan et al., 2011). Similar clinical observation was made in carcinomas of ovary cancer (Coffelt et al., 2008), breast (Heilborn et al., 2005) and lung cancers (von Haussen et al., 2008). Although LL-37 is normally cleaved from its precursor, human cathelicidin antimicrobial protein-18 (hCAP-18), by neutrophil protease 3 to become activated, evidence suggests cancer cells also produce an enzyme to proteolytically cleave their secreted hCAP-18 independent of neutrophils (Sorensen et al., 2001). This may explain the elevated levels of LL-37 in cancers. Although the involvement of LL-37 in cancers remains to be clarified, the property of LL-37 to augment proliferation, angiogenesis, protection from apoptosis and epithelial-mesenchymal-transition, all could serve as hallmarks of cancer and can be utilized by transformed/malignant cells to promote tumor growth and metastasis. Down regulation of LL-37 by the inventive peptide such as HB2233 may provide an effective way to reduce the level of LL-37 thus prevent cancerous cells spreading. The potential benefit may be further enhanced in combination with cancer drugs.

Infection with bacteria may cause sepsis and lead to septic shock, characterized by refractory hypotension and eventually multiorgan failure and death (Ulevitvh et al., 1995). Gram-positive sepsis has been recognized as an important clinical condition (Ulevitvh et al., 1995). Its causative agents are cell wall components of Gram-positive bacteria, like peptidoglycan (PGN) and lipoteichoic acid (LTA). In addition to septic shock LTA also is a causative agent for other inflammatory conditions. Atopic dermatitis (AD) is a common chronic inflammatory skin disease. The pathogenesis of AD is not fully understood and the level of cathelicidin (LL-37) expression and its association with disease severity of eczema has been controversial. AD patients are particularly susceptible to staphylococcal skin infections, which associate with the worsening of their skin conditions. Although the mechanisms by which staphylococcal bacteria can worsen AD are not yet clear cytokine production following direct infection or interaction with bacterial components or debris by keratinocytes or immune cells appears to play an important role (Bieber et al., 2008). *S. aureus* infections are known triggers for skin inflammation and can modulate immune responses due to either direct invasion by the bacteria or by bacterial products. Studies indicate high levels of *S. aureus* LTA on AD skin lesions (Travers et al., 2010). The wash fluid derived from AD lesions is found to induce the production IL-1β, IL-6, IL-10, and tumor necrosis factor-α by murine bone marrow-derived DC (Travers J B et al., 2010). The current inventive peptides shows high levels of binding to staphylococcal LTA in vitro and such activity may provide a promising treatment for neutralizing the toxic effect of LTA or LPS from Gram-negative bacteria released during infection or antibiotic treatment to improve conditions associated with septic shock and AD skin.

The potential of the inventive peptides to modulate TGF-β (transforming growth factor beta) expression on keratinocytes is particularly interesting. TGF-β is a pleiotropic cytokine/growth factor that regulates cell proliferation, differentiation, apoptosis, matrix remodeling, adhesion, invasion and migration. Generally, TGF-β1 can be produced by many different cell types. All TGF-β isoforms have been found to stimulate synthesis and turnover of extracellular matrix proteins by fibroblasts.

The hair follicle is an integral component of the skin, and each hair is a keratinized product of the follicle. Each and every hair follicle undergoes a cycle of activity: the hair grows to a maximum length, then growth ceases and the hair is shed and replaced. The phases of the hair growth cycle have been described as anagen, a long period of growth; catagen, the transitional period from growing to resting lasting 2 to 4 weeks; telogen, a period of inactivity lasting 2-4 months. Although direct evidence in humans is lacking, studies on mice suggest that inhibition of keratinocyte proliferation and induction of TGF-β1 production are directly linked to catagen regression (Foitzik et al., 2000). The in vitro observation that isolated, organ-cultured rat and human anagen hair follicles are growth inhibited by TGF-β1 resembles early stages of a catagen-like transformation in several aspects. The activity of SEQ ID NO 1, HB2233, to inhibit keratinocyte growth and modulation of TGF-β1 expression may suggest that the inventive peptides are of potential as therapeutic useful for hair removal of unwanted hair. In addition, the upregulation of TGF-β has also been linked to melanocyte immaturity by down regulation of MITF as well as melanogenic genes resulting in gray hair (Nishimura et al., 2010). Therefore the inventive peptides also have great potential for applications such as depigmentation of dark spot or skin lightening.

Skin tags (STs), soft fibromas, fibroepithelial polyps, or acrochordons are all alternative terms to describe a common benign skin condition, which consists of a bit of skin projecting from the surrounding skin. Histologically, STs is a polypoid lesion with overlying mildly acanthotic epidermis, a loose, edematous fibrovascular core exhibiting mild chronic inflammation and a nerveless dermis. Skin tags are considered the most common fibrous lesions of the skin. Although the exact etiology is not fully understood, A relation to obesity, diabetes mellitus, friction, acromegaly, organ transplant, human papilloma virus and other conditions has been reported (Zaher et al., 2007). Growth factors and hormones as well as their receptors have been implicated to play a significant role in skin tag formation (Safoury et al., 2010ab). The fact that skin tags are caused by factors that stimulate epidermal keratinocyte and dermal fibroblast proliferation, compounds, such as the inventive peptides, that suppress cell proliferation may be potentially useful to slow down progression and prevent the formation of skin tags.

The following examples are included to demonstrate certain preferred embodiments of the invention.

EXAMPLES

Example 1

Identification of Peptides that Stimulate Cell Migration and Scratch Wound Closure Human skin keratinocytes (ATCC CRL-2404) were grown in serum-free keratinocyte growth media supplemented with 5 ng/ml human recombinant epithelial growth factor (EGF) (Life Technologies, Grand Island, N.Y.). The cells were seeded onto 12-well plates and allowed to reach 100% confluent. The cell monolayer was starved for 24 hr then a scratch wound is made using a P200 (200 µl) pipette tip. The scratch wounds are washed and photographed at time 0. Peptide was added at final concentration of 20 µg/ml. Cells are kept in an incubator at 37° C., 5% $CO_2$ incubator with >90% humidity, except when images are being captured for a short period at room temperature. Scratch wound closure is followed after 7-8 hr treatment and the results are shown in Table 1.

TABLE 1

Stimulation of cell migration as assessed using keratinocyte scratch wound closure. After 7 hr treatment the percentage of closed area of PBS treated was taken as 100%, the peptide treated wound closure was calculated and presented as relative to that of PBS treated.

| SEQ ID NO | HB NO # | Sequence (N-C) | Percentage of scratch wound closure after 7 hrs compared to time 0 (%) | Wound closure Relative to PBS (%) | Cytotoxicity (µg/ml) |
|---|---|---|---|---|---|
| — | — | PBS | 22.22 | 100 | — |
| 1 | HB2233 | IEKM | 51.56 | 232* | >500 |
| 2 | HB2267 | VEKF | 31.00 | 139 | >500 |
| 3 | HB2270 | IEKI | 45.67 | 206* | >500 |
| 4 | HB2271 | IQKI | 50.59 | 228* | >500 |
| 5 | HB2272 | IKKW | 51.22 | 230* | >500 |
| 6 | HB2273 | IKKV | 36.67 | 165* | >500 |
| 7 | HB2274 | IKKL | 38.29 | 172* | >500 |
| 8 | HB2268 | KMG | 23.67 | 106 | >500 |

*significant

Example 2

Cytotoxicity on Normal Human Skin Keratinocytes

To make sure the peptides are not cytotoxic to the cells, normal human epidermal keratinocytes were seeded to a 96-well plate. The plate was incubated at 37° C. in the presence of 5% $CO_2$ to allow the cells to grow to >95% confluent. Peptides are diluted into stock solutions at concentrations of 50, 100, 200, and 500 μg/ml. The cell culture media are replaced with fresh media containing peptides at various concentrations then incubated at 37° C. and 5% $CO_2$ for 24 hr. At the end of treatment the cell viability was measured using MTT assay kit purchased from ATCC (Manassas Va.). The results are shown in Table 1. At the concentrations from 50 to 500 μg/ml the peptides do not changed cell viability as measured using MTT assay.

Example 3

Identification of Peptides that Stimulate Angiogenesis

The angiogenesis assay was performed using the In Vitra Angiogenesis Assay Kit purchased from Millipore. Briefly, matrix layer was prepared with ECMATRIX™ solution according to the manufacturer's instructions. The human umbilical vein endothelial cells (HUVEC) (ATCC, Manassas, Va.) were cultured in complete F12K medium (ATCC, Manassas, Va.) supplemented with 0.1 mg/ml of heparin (Sigma-Aldrich), 30 ug/ml of ECGS (Sigma-Aldrich) and 10% fetal bovine serum (ATCC, Manassas, Va.). The cells were harvested and resuspended in complete media. The peptide was mixed with cells at approximately $5 \times 10^3$-$1 \times 10^4$ cells per well in a 96-well plate prior to seeding cells onto the surface of the polymerized ECMATRIX™ solution. The plate was incubated at 30° C., 5% CO2 for up to 9-12 hr. Tube formation was inspected under an inverted light microscope periodically and pictures were taken at 3 and 5 hr intervals and assigned a numerical value to each pattern as shown below.

| Pattern | Value |
| --- | --- |
| Individual cells, well separated | 0 |
| Cells begin to migrate and align themselves | 1 |
| Capillary tubes visible, no sprouting | 2 |
| Sprouting of new capillary tubes visible | 3 |
| Closed polygons begin to form | 4 |
| Complex mesh like structures develop | 5 |

As shown in Table 2. SEQ ID NOs 1-7 significantly stimulate the capillary tube formation on human umbilical vein endothelial cells. As expected LL-37 is used as positive control and it also stimulate angiogenesis. PBS is used as negative control and cells begin to migrate and align themselves but no sprouting or closed polygons formed at 5 hr.

TABLE 2

Results of induction of new capillary tubes formation. Values ≥3 are considered as significant induction of angiogenesis

| SEQ ID NO | HB NO | Sequence | Promote tube formation 3 hrs | Promote tube formation 5 hrs |
| --- | --- | --- | --- | --- |
| — | — | PBS | 1 | 2 |
| 1 | HB2233 | IEKM | 3* | 4* |
| 2 | HB2267 | VEKF | 3* | 4* |
| 3 | HB2270 | IEKI | 3* | 4* |
| 4 | HB2271 | IQKI | 3* | 4* |
| 5 | HB2272 | IKKW | 3* | 4* |
| 6 | HB2273 | IKKV | 3* | 4* |
| 7 | HB2274 | IKKL | 3* | 4* |
| 8 | HB2268 | KMG | 1 | 2 |
| 9 | LL-37 | | 3* | 4* |

*significant

Example 4

Identification of Peptides to Block LTA Induced IL-6 Expression

*S. aureus* LTA induced IL-6 stimulation on human epidermal keratinocytes. Human keratinocytes were grown to >80% confluence in serum free keratinocyte cultural media. *S. aureus* LTA 10 ug/ml was pre-incubated with each peptide (50 μg/ml) at room temperature for 30 min then the mixture was transferred to keratinocyte culture. The treatment was allowed for 24 hrs. The supernatant was removed. After a brief spin to remove possible cell debris, the supernatant was subjected to IL-6 test using ELISA kit purchased from CellSciences (Canton, Mass.) according to the manufacturer's instructions. As shown in Table 3, SEQ ID NOs 1-7 clearly neutralize or antagonize the effect of LTA to stimulate IL-6 expression on human skin keratinocytes.

TABLE 3

Blocking LTA induced IL-6 expression on human skin keratinocytes

| SEQ ID NO | HB NO # | Sequence | IL-6 expression (arbitrary) | Percentage (%) expression relative to LTA induced IL-6 | Percent (%) Reduction of IL-6 compared to LTA treated |
|---|---|---|---|---|---|
| — | — | LTA alone | 1.248 | 100 | 0 |
| — | — | PBS (baseline) | 0.618 | — | — |
| 1 | HB2233 | IEKM + LTA | 0.558 | 44.71* | 55.29* |
| 2 | HB2267 | VEKF + LTA | 0.68 | 54.49* | 45.51* |
| 3 | HB2270 | IEKI + LTA | 0.776 | 62.18* | 37.82* |
| 4 | HB2271 | IQKI + LTA | 0.575 | 46.07* | 53.93* |
| 5 | HB2272 | IKKW + LTA | 0.527 | 42.22* | 57.78* |
| 6 | HB2273 | IKKV + LTA | 0.394 | 31.57* | 68.43* |
| 7 | HB2274 | IKKL + LTA | 0.321 | 25.72* | 74.28* |
| 8 | HB2268 | KMG + LTA | 1.023 | 81.97 | 18.03* |

*significant

Example 5

Identification of Peptides to Modulate Cell Proliferation and TGF-β Expression on Human Skin Keratinocytes Normal human skin keratinocytes (ATCC CRL-2404) were grown in serum-free keratinocyte growth media supplemented with 5 ng/ml human recombinant epithelial growth factor (EGF) (Life Technologies, Grand Island, N.Y.). The cells are examined microscopically daily. As the culture becomes 50-75% confluent, the media in the plate is aspirated and 0.25% trypsin/EDTA is added. When the cells become rounded and detached, the trypsin is neutralized by addition of fresh culture medium. Cells are then centrifuged and the pellet is resuspended in fresh culture medium. A hemacytometer is used to count the cell suspension and the total number of cells is adjusted to about 500-1000 cells per well by adding 100 μl of cell suspension to each well. Typically, the central 60 wells are used and the outer wells are filled with fresh medium to minimize evaporation. When cells attached in each well after 6-8 hr incubation, 100 μl of fresh media containing PBS or 2× the desired concentrations of peptide is added in triplicates. The microplate is then incubated at 37 degree C. and 5% $CO_2$ for 48-72 hr.

At the end of incubation cells are subjected to CYTOSCAN™ SRB cell cytotoxicity assay (GBiosciences, St. Louis, Mo.) according to manufacturer's instructions. Briefly, cells are fixed prior to suforhodamine B (SRB) staining. After extensive washing the color is solubilized using solubilization buffer. The absorbance was measured at 565 nm with a microplate reader. The results shown in Table 5 are the mean value of triplicate treatment and values over ±10% of control considered significant.

The TGF-β stimulation was performed by Sunny Biodiscovery Lab (Santa Paula, Calif.). Briefly, normal neonatal human epidermal keratinocytes were grown in cellnTec keratinocyte growth medium (Switzerland). The medium contained no TGF-β according to the medium supplier. The day of the experiment, growth medium was renewed and cells were treated with 50 μg/ml of peptide in triplicate for 72 hr. At the end of treatment the supernatant was removed, activated and quantified using LEGEND MAX™ total TGF-β1 ELISA Kit (Biolegend, Sam Diego, Calif.).

TABLE 4

Activity of the inventive peptides on cell proliferation and TGF-β production on human skin keratinocytes

| SEQ ID NO | HB NO | Sequence | Percent (%) Proliferation relative to PBS | Percent (%) TGF-β induction relative to PBS |
|---|---|---|---|---|
| — | — | PBS | 100 | 100 |
| 1 | HB2233 | IEKM | 77.54* | 125* |
| 2 | HB2267 | VEKF | 93.23 | 109 |
| 3 | HB2270 | IEKI | 86.31* | 114* |
| 4 | HB2271 | IQKI | 98.00 | 109 |
| 5 | HB2272 | IKKW | 96.46 | 95.6 |
| 6 | HB2273 | IKKV | 112 | 101 |
| 7 | HB2274 | IKKL | 96.31 | 96 |

*moderate effects

Example 6

Effect of Representative Peptide on SOR-300-FT Human Psoriasis Tissue Construct SOR-300-FT™ tissues were transferred to 6-well plates containing 0.9 ml of pre-warmed assay medium and equilibrated to standard culture conditions (37° C., 5% $CO_2$) for 1 hour. After the 1 hr equilibration, the tissues were re-fed with fresh medium as follow: 1) for the 24 hr time point, tissues were feed with 0.9 ml of medium and 2) for time points >24 hr, tissues were feed with 5 ml of culture medium by placing the cell culture inserts on top of the washers (Part # EPI-WSHR, MatTek Corporation). Next, 50 µl of the test articles were applied topically to the psoriatic tissues (n=3) and the test article was added to the culture medium at the 3 concentrations chosen by the Sponsor. At times 24, and 48 hours: a) the tissues were rinsed topically 3× with 300-400 µL of PBS, b) the inserts containing the tissues were held tightly with sterile forceps and the test article was rinsed gently by immersing the insert into PBS and decant medium from insert, and c) fresh test article was re-applied to the tissue immediately after rinsing and decanting (50 µL topically). Analysis was performed at t=72 hr (3× repeat applications). cDNA was generated using the Qiagen RT2 First Strand Kit (cat#330401). Relative gene expression was measured using Qiagen RT2 SYBR Green qPCR Mastermix (cat#330502) and Qiagen RT2 primers. Analysis was carried out using Bio-Rad CFX software.

TABLE 5

Fold change in gene expression levels following treatment of HB2233 and calcipotriol on the SOR-300-FT tissue

| | Fold change | |
|---|---|---|
| Gene markers | HB2233 | Calcipotriol |
| Calgranulin C | 1.2 | −1.3 |
| LL-37 | −3.7 | 5.1 |
| GRO alpha | −1.1 | 1.3 |
| ENA-78 | −1.2 | 1.6 |
| Elafin | 1.1 | −1.4 |
| HBD-2 | 1.5 | −9.0 |
| IL-8 | 1.0 | 1.3 |
| Ki-67 | −1.3 | −1.1 |
| P63 | 1.2 | −1.4 |
| Psoriasin | 1.3 | −2.3 |
| SLPI | −1.3 | 2.1 |
| Transglutaminase | 1.2 | 1.5 |

Example 7

Gene Profiling Analysis on Normal Human Skin Substitutes

The 84 genes encoding extracellular matrix and adhesion molecules were analyzed using PCR arrays conducted by Sunny Biodiscovery, Inc (Santa Paula, Calif.) Briefly, EPI-DERM™ skin substitutes (Cat.#EPI-212) were obtained from MatTek (Ashland, Mass.) and were handled according to the manufacturer's instructions. After overnight equilibration, the medium was changed and HB2233 (330 ug/ml) or water controls were applied atop of the skin tissue in duplicate and allowed the treatment for 24 hours. At the end of treatment tissues were collected and preserved in RNAlater solution (Ambion, Austin, Tex.). RNA was extracted and purified with Illustra mini RNAspin kit (Cat. #95017-489, GE Healthcare, Piscataway, N.J.). Purified total RNA was assessed at 260 nm and 280 nm with Agilent HP-8452A diode array spectrophotometer. The concentration of RNA was equalized across the samples and the expression of genes of interest was measured by real-time quantitative PCR with BioRad iCycler iQ Detection System using PCR arrays PAHS-121A, with $1^{st}$ strand synthesis kit. SYBR Green master mix and PCR running conditions from Qiagen. Efficiency ΔΔCt method was used for quantification of results, after the normalization of gene expression to 5 housekeeping genes carried with the RT2 Profiler PCR Array Data analysis version 3.5 software. Genes were considered differentially expressed if the level of expression was reasonably high (less than 30 cycles to detect) and the modulation was 1.5 or more in each duplicate series.

TABLE 6

Selected gene expression profiling on EPIDERM ™ skin tissue treated with HB2233 vs. water treated control, represented as fold change

| Gene Symbol | Description | Fold change |
|---|---|---|
| | STRUCTURE PROTEINS | |
| ACTA2 | Actin-α-12 | 2.57 |
| COL1A1 | Type 1 collagen α-1 | 2.08 |
| ITGA1 | Integrin α-1 | 2.08 |
| ITGA3 | Integrin α-3 | 1.82 |
| ITG5 | Integrin α-5 | 2.08 |
| ITGB5 | Integrin β-5 | 2.95 |
| | GROWTH FACTORS | |
| CTGF | Connective tissue growth factor | 3.63 |
| TGFB1 | Transforming growth factor β-1 | 3.16 |
| VEGFA | Vascular endothelial growth factor | 3.89 |
| HBEGF | Heparin-binding EGF-like growth factor | 2.75 |
| FGF2 | FIBROBLAST GROWTH FACTOR | 1.69 |
| WISP1 | WNT1 inducible signaling pathway protein 1 | 2.95 |
| WNT5A | Wingless-type MMTV integration site family, member 5A | 2.95 |
| | CHEMIKINES AND TISSUE ACTIVATORS | |
| CXCL1 | Chemokine (C-X-C) ligand 1 | 2.08 |
| CXCL11 | Chemokine (C-X-C) ligand 11 | 9.58 |
| MAPK3 | Mitogen activated protein kinase 3 | 4.17 |
| PLAT | Tissue plasminogen activator | 3.63 |
| PLAUR | Plasminogen activator, urokinase receptor | 2.23 |

All of the compositions or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention.

All patents and publications identified in this application are hereby incorporated by reference in their entirety.

REFERENCES

Ayehunie S., Hedin C., et al., (2012) development and characterization of 3D psoriatic tissue model. TR#702. p 1-5. Society of investigative dermatology Meeting 2012.

Bacon K, Baggiolini M, et al., (2003) Chemokine/chemokine receptor, nomenclature. Cytokine; 21:48-9.

Behm B, Babilas P, et al., (2012) Cytokines, chemokines and growth factors in wound healing. J Eur Acad Dermatol Venereol. 26(7):812-20.

Bieber T. Atopic dermatitis. (2008) New Engl J Med. 358(14):1483-1494.

Braunstein, S, Kaplan, G, Gottlieb, A B, et al: GM-CSF activates regenerative epidermal growth and stimulates keratinocyte proliferation in human skin in vivo. *J Invest Dermatol* 1994, 103:601-604.

Coffelt S B, Waterman R S, et al., (2008). Ovarian cancers overexpress the antimicrobial protein hCAP-18 and its derivative LL-37 increases ovarian cancer cell proliferation and invasion. Int J Cancer. 2008; 122(5):1030-1039.

Dombrowski Y, Schauber J, (2012). Cathelicidin LL-37: a defense molecule with a potential role in psoriasis pathogenesis. Exp Dermatol. 21(5):327-30.

Enoch S, and Price P (2004). Cellular, molecular and biochemical differences in the pathophysiology of healing between acute wounds, chrnic wounds and wounds in the aged. World Wide Wounds. (worldwidewounds.com/2004/august/Enoch/Pathophysiology-Of-Healing.html).

Foitzik K, Lindner G, et al., (2000). Control of murine hair follicle regression (catagen) by TGF-β1 in vivo. FASEB J. 14:752-760.

Folkman J, Shing Y (1992). Review Angiogenesis. J Biol Chem. 1992 Jun. 5; 267(16):10931-4.

Galiano R D, Tepper O M, Pelo C R, et al., (2004). Topical vascular endothelial growth factor accelerates diabetic wound healing through increased angiogenesis and by mobilizing and recruiting bone marrow-derived cells. Am J Pathol. June; 164(6):1935-47.

Ganguly D, Chamilos G, Lande R, et al., (2009). Self-RNA-antimicrobial peptide complexes activate human dendritic cells through TLR7 and TLR8. J Exp Med. August 31; 206(9):1983-94.

Gangavarapu P, Rajagopalan L, Kolli D, et al., (2012). The monomer-dimer equilibrium and glycosaminoglycan interactions of chemokine CXCL8 regulate tissue-specific neutrophil recruitment. J Leukoc Biol. 91(2):259-65.

Gilliet M and Lande R (2008). Antimicrobial peptides and self-DNA in autoimmune skin inflammation. Curr Opin Immunol. 20(4):401-7.

Gillitzer R and Goebeler M (2001). Review Chemokines in cutaneous wound healing. J Leukoc Biol. 69(4):513-21.

Handel T M, Johnson Z, Crown S E, et al., (2005). Review Regulation of protein function by glycosaminoglycans—as exemplified by chemokines. Annu Rev Biochem.; 74:385-410.

Harsha A, Stojadinovic O, Brem H, et al., (2008). ADAM12: a potential target for the treatment of chronic wounds. J Mol Med (Berl). 86(8):961-9.

Heilborn J D, Nilsson M F, et al., (2005). Antimicrobial protein hCAP18/LL-37 is highly expressed in breast cancer and is a putative growth factor for epithelial cells. Int J Cancer. 114(5):713-719.

Hoffmann M H, Bruns H, et al., (2012). The cathelicidins LL-37 and rCRAMP are associated with pathogenic events of arthritis in humans and rats. Ann Rheum Dis. 2012 Nov. 29. [Epub ahead of print]

Kaplan, G, Walsh, G, Guido, L S, et al: Novel responses of human skin to intradermal recombinant granulocyte/macrophage-colony-stimulating factor: Langerhans cell recruitment, keratinocyte growth, and enhanced wound healing. *J Exp Med* 1992, 175:1717-1728.

Keeley E C, Mehrad B, and Strieter R M (2008). Chemokines as mediators of neovascularization. Arterioscler Thromb Vasc Biol. 28(11):1928-36.

Keeley E C, Mehrad B, Strieter R M (2011). Chemokines as mediators of tumor angiogenesis and neovascularization. Exp Cell Res. 317(5):685-90.

Key K (2003). Arrest chemokines. Microcirculation; 10:289-95.

Mann A, Breuhahn K, Schirmacher P, Blessing M. Keratinocyte-derived granulocyte-macrophage colony stimulating factor accelerates wound healing: Stimulation of keratinocyte proliferation, granulation tissue formation, and vascularization. J Invest Dermatol. 2001 December; 117(6):1382-90.

Lin H Y, Tang C H, et al., (2010). Peptidoglycan enhances proinflammatory cytokine expression through the TLR2 receptor, MyD88, phosphatidylinositol 3-kinase/AKT and NF-kappaB pathways in BV-2 microglia. Int Immunopharmacol. 10(8):883-91.

Lowes M A, Bowcock A M, Krueger J G (2007). Review Pathogenesis and therapy of psoriasis. Nature. 445(7130): 866-73.

Nishimura E K, Suzuki M, et al., (2010). Key roles for transforming growth factor beta in melanocyte stem cell maintenance. Cell Stem Cell. 6(2):130-40.

Ono S J, Nakamura T et al., (2003). Chemokines: roles in leukocyte development, trafficking, and effector function. J Allergy Clin Immunol. 111:1185-99.

Proudfoot A E (2006). The biological relevance of chemokine-proteoglycan interactions. Biochem Soc Trans. 34(Pt 3):422-6.

Raman D, Sobolik-Delmaire T, Richmond A (2011). Chemokines in health and disease. Exp Cell Res. 317(5): 575-89.

Rees, R S, Robson, M C, Smiell, J M, Perry, BH: Becaplermin gel in the treatment of pressure ulcers: a phase II randomized, double-blind, placebo-controlled study. *Wound Repair Regen* 1999, 7:141-147, Rogalski C et al., (2002). Extensive striae distensae as a result of topical corticosteroid therapy. Acta Derm Venereol, 83:54-55

Romagnani P, Lasagni L, Annunziato F, et al., (2004). Review CXC chemokines: the regulatory link between inflammation and angiogenesis. Trends Immunol. 25(4): 201-9.

Rossi D, and Zlotnik A (2000). The biology of chemokines and their receptors. Annu Rev Immunol. 18:217-42.

Safoury O El, M Fawzi, et al., (2010a). Increased tissue leptin hormone level and mast cell count in skin tags: A possible role of adipoimmune in the growth of benign skin growths. Indian J Dermatol Venereol Leprol. 76 (5):538-542.

Safoury O El, Rashid L, and Ibrahim M, (2010b). A study of androgen and estrogen receptors α, β in skin tags. Indian J Dermatol. 2010 55(1): 20-24.

Stagno, F, Guglielmo, P, Consoli, U, Fiumara, P, Russo, M, Giustolisi, R: Successful healing of hydroxyurea-related leg ulcers with topical granulocyte-macrophage colony-stimulating factor. *Blood* 1999, 94:1479-1480.

Sørensen O E, Follin P, Johnsen et al., (2001). Human cathelicidin, hCAP-18 is processed to the antimicrobial peptide LL-37 by extracellular cleavage with proteinase 3. Blood. 97 (12):3951-3959.

Sun C L., Zhang F Z et al., (2011). LL-37 expression in the skin in systemic lupus erythematosus. Lupus. 20(9):904-11.

Travers J B, Kozman A, Mousdicas N, et al., (2010). Infected atopic dermatitis lesions contain pharmacologic amounts of lipoteichoic acid. J Allergy Clin Immunol. 125(1):146-52.

Ulevitch R J, Tobias P S, (1995). Receptor-dependent mechanisms of cell stimulation by bacterial endotoxin. Annu Rev Immunol. 1995; 13:437-57.

von Haussen J, Koczulla R, et al., (2008). The host defence peptide LL-37/hCAP-18 is a growth factor for lung cancer cells. Lung Cancer. 59(1):12-23.

Voskaridou, E, Kyrtsonis, M C, Loutradi-Anagnostou, A: Healing of chronic leg ulcers in the hemoglobinopathies with perilesional injections of granulocyte-macrophage colony-stimulating factor. Blood 1999, 93:3568-3569, Wheeler H, Black J, Webb S, Shen H, (2012). Dehiscence of corticosteroid-induced abdominal striae in a 14-year-old boy treated with bevacizumab for recurrent glioblastoma. J Child NeuroL. 27(7):927-9.

Kenshi Yamasaki, Richard L. Gallo, (2009). The molecular pathology of rosacea. Published in final edited form as: J Dermatol Sci. 55(2): 77-81.

Yamasaki K, Gallo R L (2011). Rosacea as a disease of cathelicidins and skin innate immunity. J Investig Dermatol Symp Proc. December; 15(1):12-5.

Yamasaki K, Di Nardo A, Bardan A, et al., (2007). Increased serine protease activity and cathelicidin promotes skin inflammation in rosacea. Nat Med. 13(8):975-80.

Zaher H, El Safoury O S, El Komy M M, et al., (2007). Mahmoud S B, Abd El Hamid H. Study of mast cell count in skin tags. Indian J Dermatol. 52:184-7.

What is claimed is:

1. An isolated tetrapeptide exhibiting wound repair and regeneration activity consisting of the peptide sequence of SEQ ID NO: 1 (IEKM), SEQ ID NO:2 (VEKF), SEQ ID NO:3 (IEKI), SEQ ID NO:4 (IQKI), SEQ ID NO:5 (IKKW), SEQ ID NO:6 (IKKV), or SEQ ID NO:7 (IKKL), wherein the C-terminus is in free acid form and the N-terminus is lipidated or not modified.

2. The tetrapeptide of claim 1 which comprises either or both L- and D-amino acid enantiomers.

3. A composition comprising at least one tetrapeptide according to claim 1 and a pharmaceutically acceptable carrier.

4. The composition of claim 3, wherein the tetrapeptide is present in a concentration ranging from about 0.1 μg/mL to about 500 μg/mL, or about 0.1μg/mL to about 20 mg/mL.

5. The composition of claim 3, wherein the composition is in the form of an aerosol, emulsion, liquid, lotion, solution, gel, micro-encapsulation, cream, paste, ointment, powder or foam or is incorporated in a device adapted for application to the surface of skin or under the skin tissue.

6. A method for treating a wound of the skin or treating an inflammatory condition of the skin in a mammal comprising administering to the skin or associated mucosal tissue of the mammal an effective amount of a composition comprising a pharmaceutically acceptable carrier and at least one tetrapeptide according claim 1.

7. The method of claim 6 wherein the tetrapeptide comprises either or both L- and D-amino acid enantiomers.

8. The method of claim 6, wherein the wound is due to an abrasion, blister, burn, laceration, ulcer, bruise, rash, striae distensae, scar, stretch mark or the effects of aging or environmental exposure, or the inflammatory condition is due to psoriasis, atopic dermatitis or rosacea.

9. A method of manufacturing a medicament for treating a wound or inflammatory condition of skin or associated mucosal tissue comprising combining the tetrapeptide of claim 1 with a pharmaceutically acceptable carrier.

10. The method of claim 9, wherein the wound is due to an abrasion, blister, burn, laceration, ulcer, bruise, rash, striae distensae, scar, stretch mark, or the effects of aging or environmental exposure.

11. The method of claim 9, wherein the inflammatory condition is due to psoriasis, atopic dermatitis, or rosacea.

* * * * *